(12) United States Patent
Edwards et al.

(10) Patent No.: US 10,271,735 B2
(45) Date of Patent: Apr. 30, 2019

(54) INVESTIGATION OF PHYSICAL PROPERTIES OF AN OBJECT

(71) Applicant: Isis Innovation Limited, Oxford (GB)

(72) Inventors: David John Edwards, Oxfordshire (GB); Grahame Edward Faulkner, Oxfordshire (GB); Ning Zhang, Oxfordshire (GB); Eleanor Georgina Edwards, Oxfordshire (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 954 days.

(21) Appl. No.: 14/436,837

(22) PCT Filed: Oct. 15, 2013

(86) PCT No.: PCT/GB2013/052691
§ 371 (c)(1),
(2) Date: Apr. 17, 2015

(87) PCT Pub. No.: WO2014/064425
PCT Pub. Date: May 1, 2014

(65) Prior Publication Data
US 2015/0265158 A1    Sep. 24, 2015

(30) Foreign Application Priority Data
Oct. 22, 2012 (GB) .................................. 1218931.2

(51) Int. Cl.
*A61B 5/00* (2006.01)
*G01N 22/00* (2006.01)
*A61B 5/05* (2006.01)

(52) U.S. Cl.
CPC .......... *A61B 5/0097* (2013.01); *A61B 5/0507* (2013.01); *A61B 5/7278* (2013.01);
(Continued)

(58) Field of Classification Search
CPC ... A61B 5/0097; A61B 5/7278; A61B 5/0507; A61B 2576/00; A61B 2503/40; A61B 2562/164; G01N 22/00
See application file for complete search history.

(56) References Cited

U.S. PATENT DOCUMENTS

2009/0316854 A1   12/2009   Ismail et al.
2010/0063240 A1   3/2010    Graham
(Continued)

FOREIGN PATENT DOCUMENTS

| EP | 1810019 A1 | 7/2007 |
|---|---|---|
| WO | 2010043851 A1 | 4/2010 |
| WO | 2013041856 A1 | 3/2013 |

OTHER PUBLICATIONS

Smith et al., "Loop Antennas", Antenna Engineering Handbook, Jan. 1, 1993, pp. 5-1.
(Continued)

*Primary Examiner* — Joel Lamprecht
(74) *Attorney, Agent, or Firm* — Norton Rose Fulbright US LLP

(57) ABSTRACT

An imaging system for an object such as human or animal tissue applies acoustic vibrations localized in two or three dimensions and simultaneously illuminates the object with an illuminating electromagnetic wave. A transmitter or receiver is provided that has an antenna with at least one coil that surrounds an axis along which at least a portion of the acoustic vibration is output.

19 Claims, 6 Drawing Sheets

(52) U.S. Cl.
CPC .......... *G01N 22/00* (2013.01); *A61B 2503/40* (2013.01); *A61B 2562/164* (2013.01); *A61B 2576/00* (2013.01)

(56) References Cited

U.S. PATENT DOCUMENTS

2010/0162818 A1   7/2010   David et al.
2011/0237956 A1*  9/2011   Edwards ............. A61B 5/0048
                                                        600/473

OTHER PUBLICATIONS

Max Born, Emil Wolf, Principle of Optics, Perganton Press, 1975.
G. Benedek, T. Greytak, "Brillouin Scattering in Liquids," Proceedings of the IEEE, pp. 1623-1629, 1965.
G. Peters, "History of RASS and its Use for Turbulence Measurements", IEEE, pp. 1183-1185, 2000.
E. Max North, Allen M.Peterson, "RASS, A Remote Sensing System for Measuring Low-Level Temperature Profiles," Bulletin of the American Meteorological Society, vol. 54, No. 9, pp. 912-918, 1973.
W. M. Angevine, "Radio Acoustic Sounding System (RASS) Applications and Limitations," Proceedings of IEEE, pp. 1180-1182, 2000.
K. J. Taylor, "Absolute Calibration of Microphones by a Laser-Doppler Technique," Acoustical Society of America, pp. 939-945, 1981.
Pete D.Theobald, Stephen P. Robinson, Alex D. Thompson, Roy C. Preston, "Technique for the Calibration of Hydrophones in the Frequency Range 10-600 kHz using a Heterodyne Interferometer and an Acoustically Compliant Membrane," Journal of Acoustical Society of America, pp. 3110-3116, 2005.
D. R. Bacon, "Primary Calibration of Ultrasounic Hydrophones Using Optical Interferometry," IEEE Transactions on Ultrasonic Hydrophones Using Optical Interferometry, pp. 152-161, 1988.
Waymond R. Scott, James S. Martin, "Experimental Investigation of the Acousto-Electromagnetic Sensor for Locating Land Mines," Proceedings of SPIE, vol. 3710, 1999.
Waymond R Scott, James S.Martin, "A Hybrid Acoustic/Electromagnetic Technique for Locating Land Mines," IEEE, 1998.
Waymond R.Scott, Jr. James S. Martin, "An Experimental Model of a Acousto-Electromagnetic Sensor for Detecting Land Mine," in Proceedings of the 1998 IEEE Antennas and Propagation Symposium, Atlanta, 1998.
Kamal Sarabandi, Daniel E.Lawrence, "Acoustic and Electromagnetic Wave Interaction: Estimation of Doppler Spectrum From an Acoustically Vibrated Metallic Circular Cylinder," IEEE Transactions on Antennas and Propagation, pp. 1499-1507, 2003.
Daniel E.Lawrence, Kamal Sarabandi, "Acoustic and Electromagnetic Wave Interaction: Analytical Formulation for Acousto-Electromagnetic Scattering Behavior of a Dielectric Cylinder," IEEE Transactions on Antennas and Propagation, pp. 1382-1392, 2001.
Min Zhao, J. D. Shea, S. Hagness, D. W. van der Weide, B. D. Van Veen, T.Varghese, "Numerical Study of Microwave Scattering in Breast Tissue via Coupled Dielectric and Elastic Contrast," IEEE Antennas and Wireless Propagation Letters, vol. 7, pp. 247-250, 2008.
J. G.Abbott, "Rationale and Derivation of MI and TI—a Review," Ultrasound in Medicine and Biology, vol. 25, pp. 431-438, 1999.
F. A.Duck, "Medical and Non-medical Protection Standards for Ultrasound and Infrasound," Progress in Biophysics and Molecular Biology, pp. 176-191, 2007.
Seung-Ho Lee, Waymond R.Scott, Jr, "Beamforming Array for Detecting Buried Land Mines," in SPIE, AeroSence, Detection and Remediation Technologies for Mines and Minelike Targets IV, 1999.
Seung-Ho Lee, Waymond R.Scott, Jr, "Near-field Beamforming Array for Detecting Elastic Waves in the Earth," in Detection and Remediation Technologies for Mines and Minelike Targets V, 2000.
A.H.Hussein, H.H.Abdullah, A.M.Salem,"Optimum Design of Linear Antenna Arrays Using a Hybrid MoM/GA Algorithm," IEEE Antennas and Wireless Propagation Letters, vol. 10, pp. 1232-1235, 2011.
J.Michael Johnson, Yahya Rahmat-Samii, "Genetic Algorithms and Method of Moments (GA/MOM) for the Design of Integrated Antennas," IEEE Transactions on Antennas and Propagation, vol. 47, pp. 1606-1614, 1999.
D.Yu, D.Y.Su D.M.Fu, "Genetic Algorithms and Method of Moments for the Design of PIFAS," Progress in Electromagnetics Research Letters, vol. 1, pp. 9-18, 2008.
D.Yau, "A Genetic Algorithm/Method of Moments Approach to the Optimization of an RF Coil for MRI Applications—Theoretical Considerations," Progress in Electromagnetics Research, PIER39, pp. 177-192, 2003.
A Cleveland, N Zhang and D Edwards, "Electromagnetic-Acoustic (EMA) imaging of stiffness and dielectric properties in gels", ICA, 2013.

\* cited by examiner

INVESTIGATION OF PHYSICAL PROPERTIES OF AN OBJECT

CROSS-REFERENCE TO RELATED APPLICATIONS

This application is a national phase application under 35 U.S.C. § 371 that claims priority to International Application No. PCT/GB2013/052691 filed Oct. 15, 2013, which claims the benefit of priority to Great Britain Patent Application No. 1218931.2 filed on Oct. 22, 2012, both of which are incorporated herein by reference in their entirety.

The present invention relates to the investigation of physical properties of an object. It has application in the field of imaging although not exclusively.

Various methods for investigating the physical properties of an object are known. For example there are a wide range of imaging techniques which produce an image of an object representing its physical properties. For example in the field of medical imaging, established and widely used imaging methods include x-ray radiography, computed tomography (CT), ultrasound imaging, magnetic resonance imaging (MRI), positron emission tomography (PET).

Different imaging methods are based on different physical phenomena. For example in x-ray radiography and computed tomography (CT) x-rays interact with the object, in ultrasound imaging ultrasound interacts with the object, and so on. As a result different imaging techniques produce images of different physical characteristics of the object being imaged and different imaging techniques have different advantages and limitations.

The choice of modality depends on the properties of the tissue being interrogated, for example x-rays may be suitable for high hard and calcified tissues, MRI for soft tissues and ultrasound for imaging changes in mechanical properties.

By way of example, comparing both of the common medical imaging methods of ultrasound imaging and MRI provide relatively high resolution images, but ultrasound imaging provides images of acoustic or mechanical properties whereas MRI provides images of electromagnetic properties. Thus MRI provides a useful contrast mechanism that is particularly useful in the medical imaging field because it shows essentially dielectric differences present in many tissue types. Conversely MRI suffers from the problems of being relatively expensive and of requiring powerful magnets.

Also, there are a range of spectroscopic techniques based on different physical phenomena. Such spectroscopic techniques do not necessarily produce an image but provide data in respect of a range of frequencies or wavelengths, for example of electromagnetic radiation.

In the medical sphere there is a growing field of imaging systems based on dielectric contrast that provide additional information for clinicians in determining tissue types, typically in conjunction with ultrasound and x-rays. One proposed method is microwave imaging, which has been under active research since 1998.

Ultra wideband radar systems have also been investigated to provide balance between attenuation and resolution. This type of approach has been changed to produce good quality images, but only recently have there been developed image reconstruction algorithms which approach the potential resolution of this approach.

Due to the different physical phenomena on which they are based, such different imaging techniques and different spectroscopic techniques have different applications, depending on the nature of the features of interest in the object.

WO-2010/043851 discloses a further type of imaging that may be referred to as being acousto-electromagnetic in that it involves applying acoustic vibration to an object simultaneously with illuminating the object with an illuminating electromagnetic wave.

The vibration of the object scatters and modulates the illuminating electromagnetic wave, generating a scattered electromagnetic wave including Doppler components shifted from the frequency of the illuminating electromagnetic wave by frequencies of the vibration of the object under the acoustic vibration and multiples thereof. The received scattered wave is received and data representing characteristics of the Doppler components such as amplitude and phase is derived. The detected characteristics are dependent on the mechanical response of the object and on the electromagnetic properties of the object, which cause an interaction with the illuminating electromagnetic wave. Thus the detected characteristics provide information on electromagnetic properties similar to MRI imaging but without requiring magnets.

However, the method disclosed in WO-2010/043851 makes use of acoustic vibration that is localized in a region of the object, for example using similar techniques to known ultrasound imaging. This means that the method provides information from just that region, because that is where the scattered Doppler components are generated. As a result, the resolution of the imaging is similar to that achieved by ultrasound imaging, being limited by the localization achievable on the basis of the wavelength of the acoustic vibration.

This combination of providing information on electromagnetic properties, with a resolution derived from acoustic vibration offers advantages that may provide effective imaging in a range of fields.

A challenge with acousto-electromagnetic imaging is simultaneously achieving a high resolution and a high signal-to-noise ratio. There are many, often conflicting, factors that influence these properties, making optimization difficult. It is possible for example to vary the nature of the acoustic vibration and the configuration of the apparatus for producing the acoustic vibration. The nature of the illuminating electromagnetic wave and the apparatus for generating and receiving the electromagnetic wave can also be varied. Optimization is further complicated by the constraints imposed by the context, for example a clinical context, within which the device is to be used. For example, in the case of imaging objects within a human or animal body it is important to provide a device that is convenient for a clinician to use and which can be positioned appropriately relative to the human or animal being investigated.

It is an objection of the invention to address one or more of the above-mentioned problems in the prior art. In particular, it is an object of the invention to provide an improved system and corresponding method for investigating physical properties of an object in which an acousto-electromagnetic image can be obtained with higher accuracy, reliability and/or convenience.

According to an aspect of the invention, there is provided a system for investigating physical properties of an object, the system comprising: an acoustic transducer apparatus arranged to apply to the object acoustic vibration localized in two or three dimensions in a region in the object; a transmitter arrangement arranged to illuminate the object with an illuminating electromagnetic wave having a frequency in a range extending down from 30 THz simultaneously with the application of acoustic vibration, the vibration direction of the acoustic vibration having a component parallel to the propagation direction of the illuminating electromagnetic wave so that the vibration of the object caused by the acoustic vibration in the region generates a scattered electromagnetic wave including a set of Doppler components shifted from the frequency of the illuminating electromagnetic wave by frequencies of the vibration of the object caused by the acoustic vibration and multiples thereof; a receiver arrangement arranged to receive the scattered electromagnetic wave generated in the region; and a signal processing apparatus arranged to derive, from the received scattered electromagnetic wave generated in the region, data representing at least one characteristic of the Doppler components, wherein the transmitter arrangement or the receiver arrangement comprises an antenna coil surrounding, through at least 180 degrees, an axis along which at least a portion of the acoustic vibration from the acoustic transducer apparatus is output.

Thus, a system for investigating physical properties of an object using acousto-electromagnetic imaging is provided in which the electromagnetic wave is generated or received using a coil that surrounds an axis along which acoustic vibrations are output through at least 180 degrees. In line with the normal use of the term "axis", the axis along which the acoustic vibrations are output is a mathematical construction consisting of an infinitely long, continuous line extending both in front of the acoustic transducer apparatus and behind. Obviously, the output from the acoustic transducer apparatus will only lie on the part of the axis that is in front of the acoustic transducer apparatus. However, the part of the surrounding coil may be located at an axial position that is behind the acoustic transducer apparatus and therefore "surrounds" (by at least 180 degrees) a portion of the axis that is behind the transducer apparatus.

In an embodiment the surrounding coil comprises a closed loop and the axis along which the acoustic vibrations are output passes through the inside of the closed loop. In alternative embodiments, the surrounding coil comprises a closed loop and the axis along which the acoustic vibrations are output passes outside of the closed loop (e.g. the closed loop bends around the axis in the manner of the outline of a letter C or the outline of a horse-shoe).

The requirement for the coil to surround the axis through at least 180 degrees is such that a half plane starting from the axis can be rotated about the axis through a range of angles of at least 180 degrees whilst maintaining at least one intersection with the coil. For a given angle of the half plane a single intersection will typically be made in the case where the coil forms a closed loop and the axis along which the acoustic vibrations are output passes through the closed loop, and two intersections will typically be made in the case where the coil forms a closed loop and the axis along which the acoustic vibrations are output passes outside of the closed loop.

Optionally, the coil surrounds the axis through at least 270 degrees, optionally at least 350 degrees, optionally at least 359 degrees, optionally substantially 360 degrees.

The aperture of the coil serves to intercept and/or generate the magnetic field lines of the incident/transmitted electromagnetic waves. In an embodiment the presence of the aperture is exploited to locate the acoustic transducer apparatus in a manner that improves compactness and efficiency. This facilitates alignment of the "look direction" of the transmitter and/or receiver with that of the acoustic transducer for example. In embodiments where the axis along which acoustic vibrations are output passes outside of the closed loop of the coil, wrapping the coil around the axis so that it surrounds the axis through at least 180 degrees also increases the extent to which the look direction of the transmitter and/or receiver is aligned with that of the acoustic transducer. Aligning the look direction of the transmitter and/or receiver with the look direction of the acoustic transducer maximizes the received Doppler return signal because the motion induced by the acoustic vibration is more parallel to the incident electromagnetic wave. Signal-to-noise is thereby improved relative to arrangements in which the transmitter and/or receiver arrangement is/are not aligned with the acoustic transducer apparatus in this way, for example where the transmitter and/or receiver arrangements are provided entirely to one side of the acoustic transducer apparatus.

In an embodiment the coil is provided with a single turn. In other embodiments, the coil has multiple turns.

In an embodiment, the coil is common to both the transmitter arrangement and the receiver arrangement. This configuration further enhances compactness.

In an embodiment, the coil comprises at least two conductor sections connected together by a capacitor. In an embodiment, the conductor sections and capacitors are arranged alternately around a loop, for example circumferentially. The use of conductor sections in series with capacitors allows the physical size of the coil to be greatly reduced while keep the operating frequency within a desired frequency range (typically in the tens or hundreds of megahertz for example).

In an embodiment, the coil comprises a conducting section having a thickness that is smaller in a direction parallel to the average output direction of acoustic vibration than perpendicular to the average output direction of acoustic vibration. The cross-section of the conducting section may therefore appear relatively flat, for example in the manner of a tape. This configuration provides a relatively high cross-sectional area, and thus high conductivity and therefore efficiency, without the thickness of the coil in the output direction of acoustic vibration becoming too large. Such a coil can also be positioned more effectively against the surface of the body containing the object to be imaged. The average separation between the surface of the body and the material of the coil is reduced. In certain applications it may be preferred to fix (for example glue) the coil to the body, which is also facilitated by providing a coil that is relatively flat in the direction perpendicular to the output direction of acoustic vibration.

In an embodiment, the coil is fixedly connected to the acoustic transducer apparatus. This facilitates fixing of the relative position of the coil with respect to the acoustic transducer apparatus, which may improve reliability, for example by minimizing the risk of misalignment between the acoustic vibration and the electromagnetic wave. In addition, the fixing facilitates incorporation into a device that is easy for a clinician to manipulate, such as a handheld device.

The coil can be planar or non-planar. The coil can have one of various different shapes when viewed along the direction of output of acoustic vibration, for example substantially circular, substantially oval, substantially ellipsoidal, substantially polygonal. The coil may comprise a continuous closed loop of conductor (at least when viewed along the axis along which acoustic vibration is output). Alternatively, the coil may comprise a plurality of conductor sections connected together by capacitors or other electrical components.

In an embodiment the selection of the acoustic vibration is optimized. The selection needs to take into account the following characteristics of the imaging. A first factor is that the choice of frequency impacts on the resolution of the imaging that may be achieved. This is because the method involves localization of the acoustic vibration in a region of the object from which the scattered Doppler components are generated. The second factor is that the magnitude of the acoustic vibration of the object is also dependent on the frequency of the acoustic vibration. This effect derives simply from the mechanical properties of the object under investigation. For some objects, these two factors can compete, requiring careful choice of the frequency of the acoustic vibration in order to balance these factors.

In an embodiment, a specific form of acoustic vibration is used that comprises a carrier wave that is modulated by an AM waveform. This acoustic vibration is optimised to provide advantages during imaging. In particular, the carrier wave is selected to provide the localization of the acoustic vibration, whereas the AM waveform is chosen to include a frequency component that provides a vibration of the object. The nature of amplitude modulation is that the carrier wave has a higher frequency than the AM waveform. Thus, the AM waveform may be selected to provide a vibration of the object of greater magnitude than the carrier wave. Thus the present invention improves the flexibility in the choice of the selection of the acoustic waveform, particularly for objects where the desired resolution requires the use of a frequency that provides a low mechanical response. For such objects, the carrier wave may be selected to optimize the resolution and the AM waveform may be independently chosen to provide a significant mechanical response.

The AM waveform may take a variety of forms. In its simplest form, the AM waveform may be a single frequency component, that is a sinusoidal waveform at a given frequency. However, other waveforms having a fundamental frequency component and harmonic frequency components may also be used, and can in some instances have the benefit of being easy to generate. For example, the AM waveform may be a square wave, which is particularly easy to generate simply by pulsing the carrier waveform on and off.

Where the AM waveform has multiple frequency components, then in principle to detect Doppler components shifted from the frequency of the illuminating electromagnetic wave i.e. frequency of any of the frequency components of the AM waveform. However, desirably there is used the fundamental frequency component the AM waveform, because this will generally provide the frequency component of the largest magnitude and will provide the maximum response. Furthermore, the fundamental frequency component is most easily isolated because it has relatively large separation from other Doppler components.

The frequency component of the AM waveform that is utilized is selected having regard to the relevant mechanical properties of the object. To optimize the response, this frequency component desirably has a period of the same order of magnitude as the acoustic relaxation time of the object in the regions under investigation.

The present invention may be applied to provide imaging of the object. In this case the acoustic vibration is applied simultaneously or sequentially in a localized manner in a plurality of regions with different amplitude modulation applied to the ultrasound excitation in each region and the scattered electromagnetic wave generated in each of the plurality of regions is received and used to derive data representing the at least one characteristic of the detected Doppler component in respect of each region as image data.

In this way, it is possible to generate image data for a plurality of regions and thus build up an image representing information on the physical properties of the object. In the case that the acoustic vibration is localized in two dimensions, then the regions extend in the third direction and thus the image is a two dimensional image (or shadow image). In the case that the acoustic vibration is localized in three dimensions, then the regions are limited in extent in that third direction and a three-dimensional image may be derived.

The acoustic vibration may be applied localized at the plurality of regions sequentially. In this case, the acoustic vibration may have the same frequency which simplifies implementation of the method but is not essential.

Alternatively, the acoustic vibration may be applied localized in the plurality of regions simultaneously but utilizing different frequency components in each region. In this case, frequency components applied to each region have different frequencies with the result that the electromagnetic waves scattered from each region have different frequencies, allowing the Doppler components simultaneously generated in respect of each region to be separated and used to derive the image data representing at least one characteristic of the Doppler components in respect of each region.

In principle, the present invention may also be used applying the acoustic vibration to just a single region without providing imaging of the object. In this case, the information on the physical properties of the object which is derived is useful nonetheless because it is based on the physical phenomenon described above.

These properties mean that the imaging of the present invention can provide advantages over the established imaging methods when applied to imaging human or animal tissue, including but not limited to medical imaging.

According to an alternative aspect of the invention, there is provided a method of investigating physical properties of an object, comprising: applying to the object acoustic vibration localized in two or three dimensions in a region in the object; illuminating the object with an illuminating electromagnetic wave having a frequency in a range extending down from 30 THz simultaneously with the application of acoustic vibration, the vibration direction of the acoustic vibration having a component parallel to the propagation direction of the illuminating electromagnetic wave so that the vibration of the object caused by the acoustic vibration in the region generates a scattered electromagnetic wave including a set of Doppler components shifted from the frequency of the illuminating electromagnetic wave by frequencies of the vibration of the object caused by the acoustic vibration and multiples thereof; receiving the scattered electromagnetic wave generated in the region; deriving, from the received scattered electromagnetic wave generated in the region, data representing at least one characteristic of the Doppler components, wherein the illuminating or receiving comprises using an antenna coil that surrounds, through at least 180 degrees, an axis along which at least a portion of the acoustic vibration from the acoustic transducer apparatus is output.

To allow better understanding, embodiments of the present invention will now be described by way of non-limitative example with reference to the accompanying drawings, in which.

Figure 1:
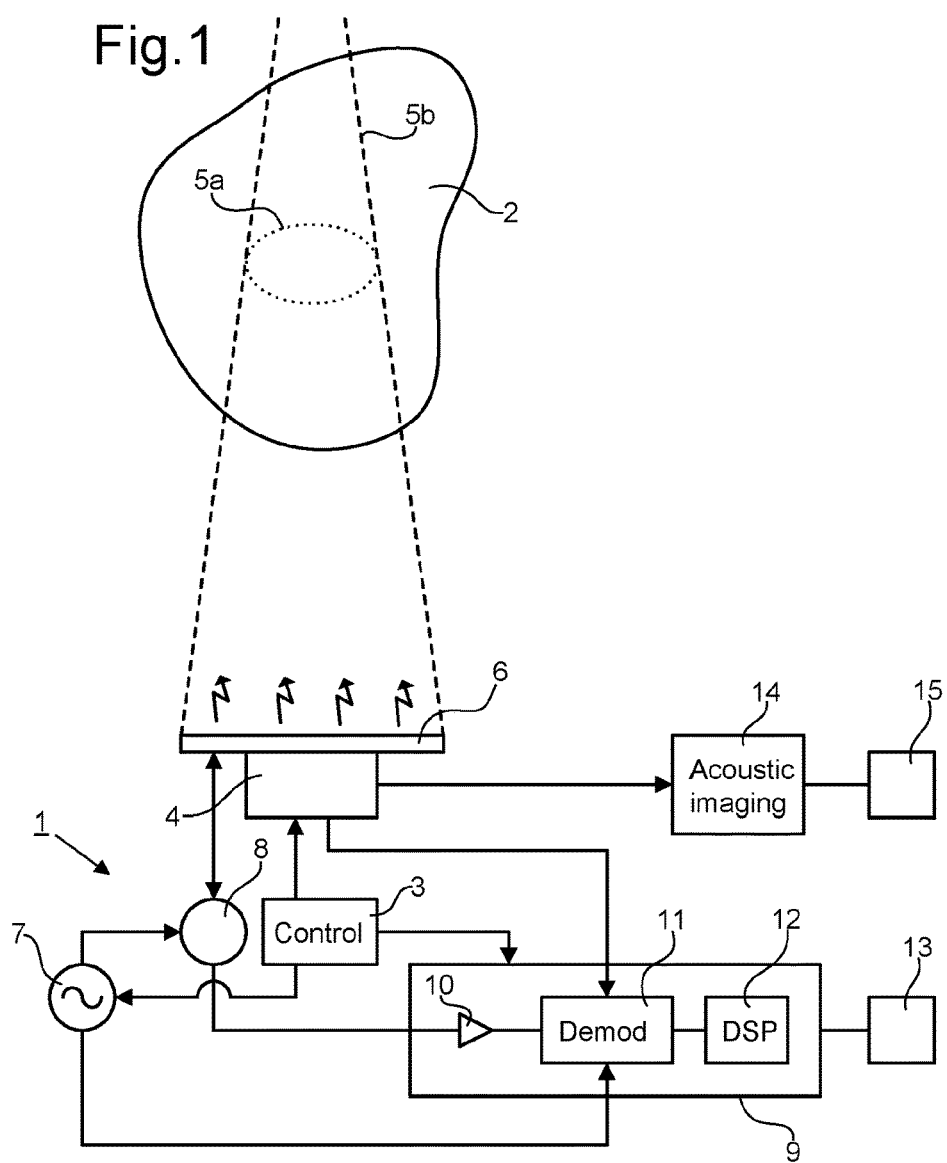
FIG. 1 is a diagram of an imaging system.

There will first be described a system 1 for investigating physical properties of an object 2, as shown in FIG. 1. The object 2 may be a biological object, for example human or animal tissue, in which case the system 1 may be applied in the field of medical imaging. However, the present invention is not restricted to that field and may be applied to a range of objects in other technical fields.

The system 1 includes a control unit 3 which controls the other components of the system 1. The control unit 3 may be implemented by a computer apparatus running an appropriate program.

The system 1 includes an acoustic transducer apparatus 4 which operates under the control of the control unit 3. The acoustic transducer apparatus 4 in operation applies acoustic vibration to the object 2.

In an embodiment, the nature of the acoustic vibration is as follows. The acoustic vibration comprises a carrier wave amplitude modulated by an AM waveform that is periodic.

Figure 2:
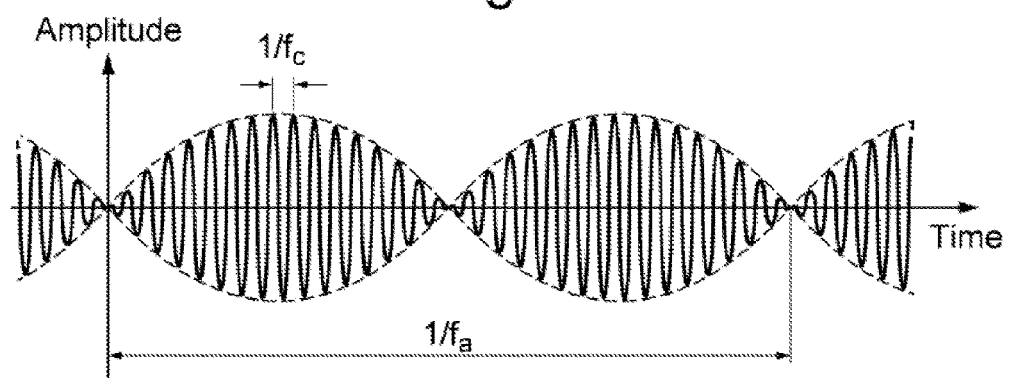
FIGS. 2 and 3 are graphs of two alternative waveforms of the acoustic vibration.
Figure 3:
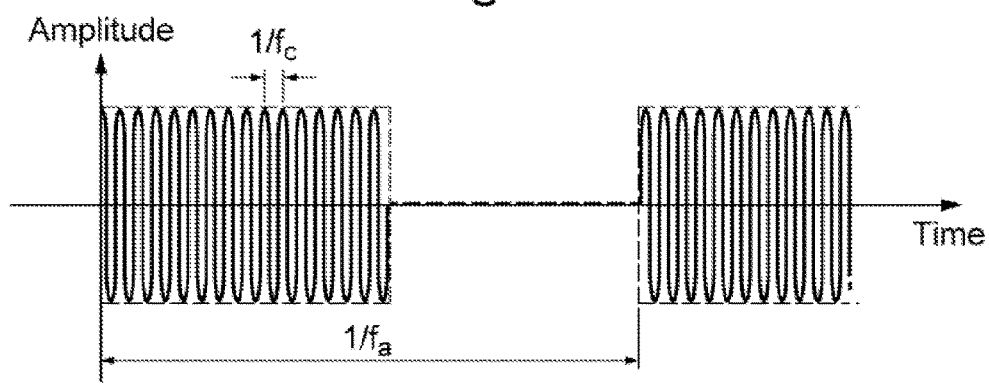

Two non-limitative examples of suitable acoustic waveforms are shown in FIGS. 2 and 3, wherein the carrier wave has in both cases a frequency fc. In FIG. 2, the AM waveform has its simplest form comprising a fundamental frequency component of frequency fa. In FIG. 3, the AM waveform is a square wave having a period of (1/fa), and hence comprising a fundamental frequency component of frequency fa and harmonic frequency components that are multiples of frequency fa.

The carrier wave is most simple to generate if it is a simple sinusoidal wave as shown in FIGS. 2 and 3, although in general, the carrier wave could have any other suitable waveform.

In general, the AM waveform may have a wide range of forms, but the use of the square wave as in the example of FIG. 3 is advantageous in that it is very easily generated by pulsing the carrier wave on and off. In the example of FIG. 3, the AM waveform is a square wave having equal on and off periods but this is not essential and it could be a square wave having unequal on and off periods. The nature of amplitude modulation is that carrier wave has a frequency that is smaller than the frequency of at least the fundamental frequency component of the AM waveform, and typically of one or more of the harmonic frequency components. In many practical embodiments, the carrier wave has a frequency that is smaller than the frequency of the fundamental frequency component of the AM waveform by at least one or two orders of magnitude.

The acoustic vibration is localized in a region 5 at a given location within the object 2. The carrier wave is selected to provide the desired localization of the acoustic vibration. The degree of localization is dependent on the wavelength, and so the frequency fc of the carrier wave is chosen accordingly.

The acoustic vibration causes vibration of the object 2 in the region 5. The AM waveform is selected to provide a vibration of the object 2 that is of greater magnitude than the carrier wave at the frequency of at least one of the frequency components of the AM waveform that is utilized, preferably the fundamental frequency component. As the carrier wave is selected to provide localization of the acoustic vibration to achieve the desired resolution, depending on the nature of object 2, the mechanical response of the object 2 might not be optimal at the frequency of the carrier wave. Thus the AM waveform is used to provide vibration of the object 2 at a lower frequency than the carrier wave, at which the magnitude of the vibration of the object 2 is greater.

In general, the method may utilize any of the frequency components of the AM waveform, but advantageously the fundamental frequency component is utilized because this generally has a larger magnitude than the harmonic frequency components, if any, and produces Doppler components of larger magnitude that are most easily separated from the scattered electromagnetic wave.

To optimize the mechanical response of the object, the frequency component of the AM waveform that is utilized, for example fa in the case of utilizing the fundamental frequency component, may be selected to have a frequency that is of the same order of magnitude as the acoustic relaxation time of the region 5 of the object 2. Such an acoustic relaxation time can be measured or derived theoretically for the type of the object 2 under investigation. Similarly, the frequency component that is utilized may be selected to have a frequency that provides a resonant vibration of the object.

For some types of object, the AM waveform may provide a vibration of the object 2, which is, at the frequency of the frequency components of the AM waveform utilized, of a magnitude that is greater than the carrier wave by one or more orders of magnitude. In such cases, the vibration of the object 2 at the frequency of the carrier wave is by comparison insignificant and may be ignored.

As alternatives that are both illustrated in FIG. 1, the acoustic vibration may be localized in two dimensions in a region 5b (shown in dashed outline) that is limited in extent perpendicular to the propagation direction of the acoustic vibration but extends along the propagation direction, or may be localized in three dimensions in a region 5a (shown in dotted outline) that is also limited along the propagation direction. The localization of the acoustic vibration may be achieved using conventional equipment as described in more detail below. When localized in three dimensions, along the direction of propagation of the acoustic wave, the acoustic vibration might be localized only instantaneously as the acoustic wave propagates. In many fields of application such as medical imaging, the acoustic vibration is ultrasonic.

In the simplest embodiment, the acoustic vibration is localized at a single location at a given time, that location being scanned over the object 2 so that the acoustic vibration is applied to regions 5 at a plurality of different regions 5 successively. Such scanning may be performed by using an acoustic transducer apparatus 4 which has a controllable focus or beam, or alternatively by physically moving the acoustic transducer apparatus 4 with fixed focus or beam, for example using a mechanical translator. The scanning may be carried out in one, two or three dimensions.

In more complicated embodiments, the acoustic vibration is localized in regions 5 at plural locations simultaneously but in this case the AM waveform of the acoustic vibration is different in different locations, as discussed further below.

The system 1 also includes a transmitter arrangement comprising an antenna coil 6 connected via a directional coupler 8, to a radio frequency source 7 controlled by the control unit 3 that supplies the antenna coil 6 with a drive signal that outputs a corresponding electromagnetic wave. Thus the transmitter arrangement in operation illuminates the object 2 with an illuminating electromagnetic wave, typically having a radio frequency, and having a sufficiently broad beam to cover the entire volume of the object 2 under investigation, ideally uniformly. The illuminating electromagnetic wave is desirably a continuous wave rather than a pulse. In this case, the illuminating electromagnetic wave has a constant amplitude and frequency, at least over the period for which the interaction with the acoustic wave is monitored by receiving the scattered Doppler components.

For ease of detection, the illuminating electromagnetic wave is predominantly of a single frequency, but in general the illuminating electromagnetic wave could include a band of frequencies. The frequency of the illuminating electromagnetic wave is greater than the frequency of the acoustic vibration, preferably by at least an order of magnitude.

The illuminating electromagnetic wave is scattered by the object 2. Within the region 5, there is an interaction between the object 2 that is vibrated by the acoustic vibration and the illuminating electromagnetic wave, which causes the acoustic vibration of the object 2 in the region 5 to modulate the scattered electromagnetic wave. In particular, the scattered electromagnetic wave that is generated includes components at the frequency of the illuminating electromagnetic wave and Doppler components at frequencies shifted from the frequency of the illuminating electromagnetic wave by frequencies of the vibration of the object and multiples thereof. This includes Doppler components at frequencies shifted from the frequency of the illuminating electromagnetic wave by frequencies of the frequency components of the AM waveform and multiples thereof. Amplitude modulation is used as described above to provide a greater magnitude of vibration at a frequency of at least one frequency component of the AM waveform than at a frequency of the carrier wave, so the Doppler components arising from the carrier wave are of lower magnitude and in many cases insignificant and may be ignored.

Figure 4A:
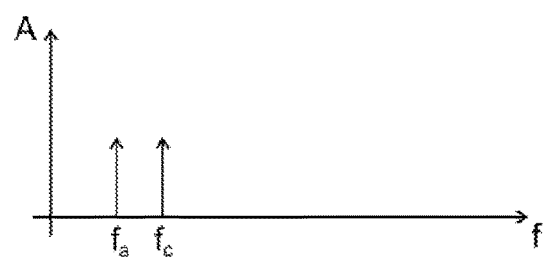
FIGS. 4a to 4c are graphs of the frequency spectrum of the acoustic vibration, the illuminating electromagnetic wave and the scattered electromagnetic wave.
Figure 4B:
Figure 4C:
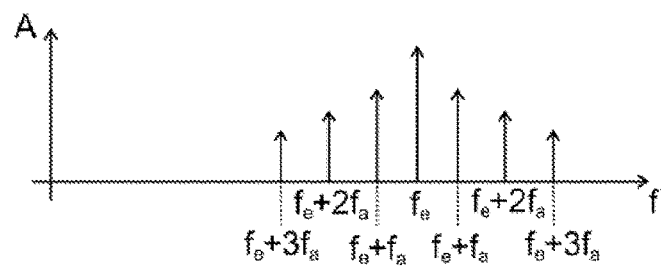

This is illustrated graphically in FIGS. 4a to 4c which are graphs of the frequency spectrum of the acoustic vibration, the illuminating electromagnetic wave and the scattered electromagnetic wave, respectively. In this example, the acoustic vibration comprises the carrier wave at a frequency fc and a fundamental frequency component of frequency fa, as shown in FIG. 2. The illuminating electromagnetic wave has a single EM frequency of fe.

The scattered electromagnetic wave comprises a central component of the EM frequency fe of the illuminating electromagnetic wave.

The scattered electromagnetic wave also comprises Doppler components (sidebands) at frequencies fe±n.fa, where n is an integer, i.e. shifted from the EM frequency fe of the illuminating electromagnetic wave by the frequency fa of the fundamental frequency component of the AM waveform and multiples thereof. Although FIG. 4c illustrates an example with three Doppler components on each side, in general there could be any number of Doppler components depending on the physical interaction. The Doppler components arising from vibration at the frequency fc of the carrier are not shown in FIG. 4c, being less significant.

Where the AM waveform also comprises harmonic frequency components, there will be further Doppler components shifted from the EM frequency fe of the illuminating electromagnetic wave by the frequency of the harmonic frequency components of the AM waveform and multiples thereof. However these further Doppler components overlap the Doppler components shown in FIG. 4c of order two or greater, and so are difficult to separate.

The physical phenomenon behind the generation of the scattered electromagnetic wave including the Doppler components is that boundaries between areas in the object 2 having different electrical properties such as conductivity and dielectric permittivity (or more generally areas where those electrical properties change) scatter the illuminating electrical magnetic wave and that vibration of those boundaries modulates the scattered wave. Thus it may be considered that the central component having the frequency of the illuminating electromagnetic wave corresponds to the scattering of the object 2 when stationary, whereas the Doppler components are generated by the vibration of the object 2.

Indeed this physical phenomenon for the general case of a vibrating object is of itself known, for example as disclosed in Lawrence et al., "Electromagnetic Scattering from Vibrating Penetrable Objects Using a General Class of Time-Varying Sheet Boundary Conditions", IEEE Transactions on Antennas and Propagation, Vol. 54, no. 7, pp. 2054-2061, July 2006. However this document merely considers the electromagnetic wave scattered by metallic and dielectric bodies which are vibrating without considering how the vibration is generated. In contrast in the present invention, the acoustic vibrations are applied localized in a region 5, meaning that the any detected Doppler components in the scattered electromagnetic wave are known to have been generated in the region 5. On this basis the system 1 uses the Doppler components to provide information about the object 2 at the location of the region 5. In particular the detected Doppler components are dependant on the mechanical response (compliance) of the object 2 at the location of the region 5 to the acoustic vibration and also on the electrical properties of the object 2 at the location of the region 5. By applying the acoustic vibration to regions 5 at different locations it is possible to build up an image of the object 2.

The system 1 also includes a receiver arrangement, which in the embodiment shown also comprises the antenna coil 6. The receiver arrangement (antenna coil 6) is connected to signal processing apparatus 9, which is controlled by the control unit 3. In this embodiment, the antenna coil 6 thus acts as a common antenna coil for both transmitter and receiver arrangements. In other embodiments, separate coils are provided respectively for the transmitter and receiver arrangements.

The antenna coil of the receiver arrangement (antenna coil 6 when a common coil is provided) is tuned to the frequency of the illuminating electromagnetic wave and is matched to the measurement medium, that is to the object 2 and/or any medium (e.g. air or an acoustic matching medium) provided between the object 2 and the antenna. In operation, the receiver antenna receives the scattered wave and supplies it to the signal processing apparatus 9 which analyses it to detect the Doppler components arising from the frequency components of the AM waveform that is utilized, and to output a signal representing the phase and amplitude of the Doppler components, or in general any characteristics of the Doppler components.

The magnitude of the scattered Doppler components is maximised by the vibration direction of the acoustic vibration being parallel to the propagation direction of the illuminating electromagnetic wave. The vibration direction is parallel to the propagation direction of the acoustic vibration, so this corresponds to the acoustic vibration and the illuminating electromagnetic wave having parallel or antiparallel directions. This is because the mechanical movement of the region 5 resolved along the propagation direction of the illuminating electromagnetic wave is greatest in this direction, ignoring secondary motions which may be induced in other directions due to mechanical distortion of bulk material. If there is an angle α between the direction of the acoustic vibration and the propagation direction of the illuminating electromagnetic wave, then the velocity of the acoustic vibration resolved along the propagation direction of the illuminating electromagnetic wave is reduced, scaling with $\cos(\alpha)$. This has the effect that the magnitude of the scattered Doppler components is similarly reduced, scaling with $\cos(\alpha)$. Effectively this means that the vibration direction of the acoustic vibration should not be perpendicular to the propagation direction of the illuminating electromagnetic wave, and is preferably parallel, although the Doppler components may still be observed with higher angles α.

In general, the receiver antenna may be located at any angle relative to the propagation direction of the electromagnetic wave and the vibration direction of the acoustic vibration. This is because the scattered Doppler components can in principle be scattered in any direction. The direction of scattering depends on the physical properties of the object 2 in the region 5.

Advantageously, the scattered electromagnetic wave is received along a line parallel or antiparallel to the propagation direction of the illuminating electromagnetic wave because the scattering is typically strong in these directions. Reception along a line antiparallel to the propagation direction of the illuminating electromagnetic wave may be achieved by the transmitter antenna and the receiver antenna being located close together (subject to the constraints imposed by their physical bulk) or being replaced by a common antenna connected to appropriate circuitry (such as a directional coupler 8) to isolate the frequency source 7 from circuitry handling the detected Doppler components.

However, the scattered electromagnetic wave may be received in other directions. Advantageously, the scattered electromagnetic wave is received in plural directions. This can provide additional information on the nature of object 2 in the region 5 because the direction of scattering depends on the physical properties of the object 2 which causes the scattering.

The selection of the acoustic vibration and the illuminating electromagnetic wave will now be discussed.

As the Doppler components are generated from the interaction caused by the acoustic vibration of the region 5, the resolution of the image data 13 is equal to the size of that region 5 as governed by the degree of localization of the acoustic vibration achieved by the acoustic transducer apparatus 5. The resolution is therefore dependent on the frequency fc of the carrier wave in a similar manner to ultrasound imaging. Thus the present imaging technique can achieve similar resolution to that achieved by ultrasound imaging. For example the resolution might be less than a millimeter at very high ultrasound acoustic frequencies (roughly speaking, 1 mm resolution corresponds to a frequency of 1 MHz, 100 µm to 10 MHz, and 1 µm to 100 MHz).

The frequency of the acoustic wave controls the resolution and is therefore chosen to be sufficiently high to achieve the desired resolution having regard to the features of interest in the object 2 being imaged. The frequency of the acoustic wave may be subject to practical constraints similar to those with conventional ultrasound imaging, such as the frequencies achievable by the acoustic transducer apparatus 4, and the penetration of the acoustic waves in the object 2 being imaged.

The frequency fc of the carrier wave is selected having regard to the desired resolution and also having regard to the depth of penetration that is achievable at different frequencies. Generally, it is necessary to balance these two factors, again in a similar manner to ultrasound imaging. Typically, the frequency fc of the carrier wave may be in a range extending from 10 kHz to 1 GHz. In the case that the object is a biological object, such as human or animal tissue, typically the frequency fc of the carrier wave may be in a range extending up from 1 MHz, preferably up from 2 MHz, and/or extending up to 50 MHz, preferably up to 10 MHz. Such frequencies are ultrasonic, although in general acoustic frequencies in the audible range could in principle be used in some fields of application.

The AM waveform of the acoustic vibration is chosen having regard to the mechanical properties of the object 5 to provide vibration of desired magnitude, in the manner discussed in detail above. Typically the frequency component of the AM waveform that is utilized, generally the fundamental frequency of the AM waveform, has a frequency in a range extending from 1 Hz to 100 MHz. In the case that the object is a biological object, such as human or animal tissue, then the frequency of the frequency component that is utilized is preferably in a range extending up from 10 kHz, preferably up from 100 kHz, and/or extending up to 1 kHz.

The EM frequency of the illuminating electromagnetic wave is selected as follows. The image contrast mechanism is different from ultrasound imaging being dependent on the physical interaction between the acoustic vibration and the illuminating electromagnetic vibration and providing information on the mechanical response (compliance) of the object 2 to the acoustic vibration and on the electrical properties of the object 2, as discussed above, for example providing similar information to MRI without the requirement for magnets. Thus the present imaging technique can be seen as an alternative to other imaging modalities. The degree of absorption of the illuminating electromagnetic wave in the object 2 increases with its frequency. Thus the frequency of the illuminating electromagnetic wave is chosen to be sufficiently low to provide absorption in the object 2 which is sufficiently low to allow the entire object 2 to be imaged.

Thus, the EM frequency is chosen having regard to the electromagnetic properties of the object 2 in order to provide useful information about the object 2. In general the illuminating electromagnetic wave is a radio wave having an EM frequency in a range extending up to 30 THz, that is in the Terahertz band or below; up to 300 GHz, that is in the EHF (Extremely High Frequency) band or below, corresponding to microwave frequencies or below; or in some fields of application up to 100 GHz. In the case that the object 2 is a biological object such as human or animal tissue, advantageously the range extends up to 100 GHz, preferably up to 2 GHz. This means that the interaction in the object 2 provides information on the electromagnetic properties of the object 2 similar to MRI imaging.

The lower limit of the EM frequency is dependent on the ability of the signal processing apparatus 9 described below to separate the Doppler components from the EM frequency, noting that there is a limit in practice on how wide an EM envelope created by the amplitude modulation that can be detected, as known in the field of wideband frequency modulation. Therefore, typically the illuminating electromagnetic wave has an EM frequency in a range extending up from a value of twice said frequency component of the AM waveform, preferably ten times said frequency component of the AM waveform.

The object 2 may have a response which varies at different frequencies. Therefore, the imaging may be performed with acoustic vibrations of different frequencies and/or with an illuminating electromagnetic wave of different frequencies. The different frequencies may be applied at different times by repeating the operation of the system 1 but adjusting the acoustic frequency. Alternatively different frequencies may be applied simultaneously to the same or different regions 5. The different frequencies of excitation can also be achieved by using pseudo random pulse sequences (such as maximal length sequences) or other spread spectrum techniques. In this way, information may be obtained in respect of the different frequencies of the acoustic vibrations and/or the illuminating electromagnetic wave, so the technique is a spectroscopic technique. This allows better characterization of the nature of the object 2.

The signal processing apparatus 9 includes an amplifier 10, a frequency-modulation (FM) demodulator 11 and a digital signal processor 12.

The amplifier 10 receives and amplifies the signal received by the receiver antenna (via directional coupler 8 in the embodiment shown, due to the receiver antenna being integrated with the transmitter antenna into common antenna 6). Due to the low SNR, the amplifier 10 is desirably a very low noise amplifier.

The amplified signal output by the amplifier 10 is supplied to an FM demodulator 11 which is arranged to detect, from the received, scattered electromagnetic wave, a Doppler component shifted from the frequency of the illuminating electromagnetic wave by the frequency of frequency component of the AM waveform utilized, typically the fundamental frequency component. The FM demodulator 11 outputs a signal representing the phase and amplitude of the Doppler component.

Figure 5:
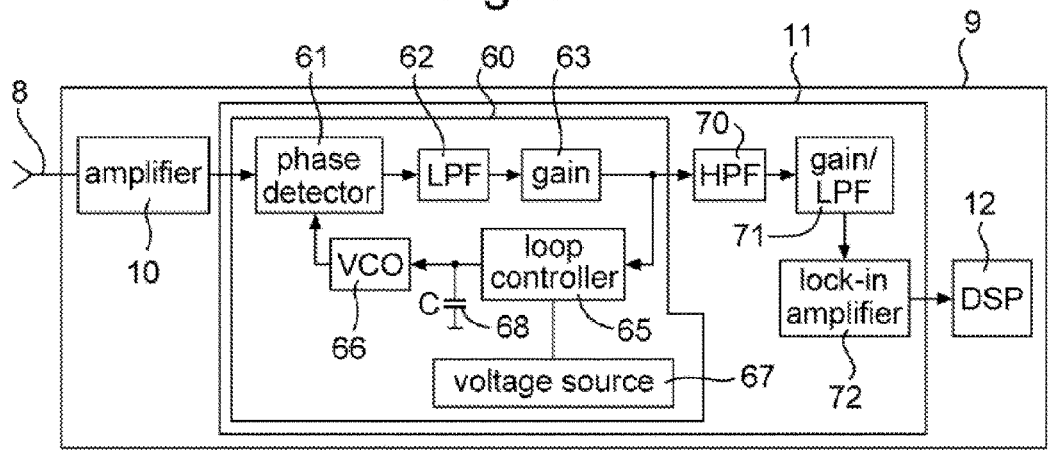
FIG. 5 is a diagram of the signal processing apparatus of the imaging system.

The FM demodulator 11 may have a detailed construction that is shown in FIG. 5 and will now be described.

The FM demodulator 11 comprises a phase-locked loop (PLL) 60 that is supplied with the scattered EM wave received by the receiver antenna, via the amplifier 10. The PLL 60 comprises a phase detector 61, a low pass filter 62, a gain stage 63, as well as a loop controller 65 and a voltage controlled oscillator (VCO) 66 connected in a negative feedback loop. As described below, the PLL 60 is locked to the EM frequency, and so the VCO 66 outputs a signal at that EM frequency. The phase detector 61 is supplied with the scattered electromagnetic wave and with the output of the VCO 66. The phase detector 61 outputs the phase error between its two input signals which is supplied through the low pass filter 62 and the gain stage 63 to form the output signal. The output signal therefore contains the frequency-demodulated signal comprising the set of Doppler components frequency-demodulated from the EM frequency.

This frequency-demodulated signal is also passed back as a feedback signal in the negative feedback loop to the loop controller 65. The loop controller 65 inverts the feedback signal before supplying it to the VCO 66, so has to control the VCO 66 to output a signal having the same EM frequency as the main component of the scattered electromagnetic wave. The loop controller 65 is therefore arranged as a Type I fixed gain controller, since this design is likely to provide a relatively low noise. The loop controller 65 also shifts the level of the feedback signal to adjust the centre frequency of the output of the VCO 66.

Two specific configurations for the PLL 60 are as follows.

The first configuration is intended to be used with an EM frequency of 790 MHz. In this first configuration:

the phase detector 61 is a Minicircuit ZX05-10L+, 10-1000 Mhz, 3 dBm, Lo DBD mixer;

the low pass filter 62 is a Minicircuit SLP-2.5+, 2.5 MHz cut off, low pass filter; and the VCO 60 is a Minicircuit ZX95-800C+, −97 dbc/Hz noise at 1 kHz, 790 MHz centre frequency.

These components are chosen for their low noise. For example, the phase detector 61 is a diode mixer that produces a negligible amount of noise, despite having a non-linear phase response.

In this first configuration, the loop controller 65 is a heavily decoupled AD797 operational amplifier in a negative feedback configuration. The loop gain is chosen to be minus 100 dB as a compromise between output noise and locked frequency range, since higher gain will increase the noise to less desirable doubles.

The voltage shifting is accomplished by referencing the non-inverting input of the loop controller 65 to a very low noise voltage source 67, for example provided by an analog device ADR445 that produces a voltage of 5V that may be devalued by a potential divider. This reference is decoupled using a large decoupling capacitor (not shown) to minimize any potential 1/f noise in its output level.

The output of the loop controller 65 is supplied to the VCO 66 through a low pass filter 68 that is a single pole low pass filter consisting of a RC circuit, in order to reduce distortion and increase stability.

During startup, the voltage source 67 is adjusted to vary the output voltage of the loop controller 65. In particular, the voltage level fluctuates as the loop controller 65 stabilizes. A more convenient method is to change the input voltage slightly (for example by the order of 5 mV), which has the same effect. The operating DC points sets the voltage of the VCO 66, which needs to correspond to the EM frequency of 790 MHz, within 10 kHz.

The feedback gain has been tested empirically to give acceptable knowledge performance. Another potential improvement is to provide two stages of amplifiers in the feedback loop, with the additional amplifier acting as a DC offset. This would allow the DC shift that needs to be corrected on startup, although at the cost of a small increase of noise levels.

A second configuration is intended to be used with an EM frequency of 434 MHz. In this second configuration:

the phase detector 61 is a Minicircuit ZX05-10 L+, 10-1000 Mhz, 3 dBm, Lo DBD mixer;

the low pass filter 65 is a Minicircuit LPF-BOR3+, 0.3 MHz cut off low pass filter; and the VCO 60 is a Crystek CVSS-940, −110 dbc/Hz noise at 1 kHz, 434 MHz centre frequency.

The second configuration the PLL 60 remains essentially the same as the first configuration, except that for a voltage regulator used to supply the VCO 66.

In this second configuration, the components are substantive to reduce noise pickup.

The VCO 66 in this configuration is a high stability crystal based oscillator with a very low phase noise, which has been found to be a significant source of noise.

The circuit has been tested with and without the low pass filter 68 on the input to the VCO 66. It has been found that a large capacitance in the low pass filter 68 improves the SNR by a small but significant amount, whilst reducing the lock range. In this second configuration, the time constant of 0.03 s has been empirically determined to be optimal.

The output of the PLL 60 is supplied to the lock-in amplifier 72, through a high pass filter 70 and a gain stage 71 that also acts as a low pass filter, so that the high pass filter 70 and gain stage 71 together act as a band pass filter. The lock-in amplifier 72 uses a reference frequency signal that a reference frequency equal to the frequency of the utilized frequency components of the AM waveform, which is typically the fundamental frequency component of the AM waveform. Thus the reference frequency is selected to be at a frequency of vibration of the object 2 caused by the acoustic vibration. By way of comparison, if the acoustic vibration were to comprise a single frequency component then the reference frequency would be the frequency of that single frequency component.

As described above, the utilized frequency component may be any of the frequency components of the AM waveform and multiples thereof, but is generally the fundamental frequency component fa of the AM waveform. The reference frequency for the PLL 60 and may be derived from a frequency source that is also used to derive the AM waveform (as described further below) and that output a signal of frequency fa. Accordingly, the acoustic transducer apparatus 4 may be connected to the FM demodulator 11 as shown in FIG. 1 to supply the AM waveform or a signal of frequency fa from the frequency source to the lock-in amplifier 72.

The lock-in amplifier 72 is arranged to extract from the frequency-demodulated signal supplied thereto a signal at the reference frequency. Thus, the lock-in amplifier 72 extracts the desired Doppler component. The lock-in amplifier 72 is further configured to generate the amplitude and phase of the extracted signal, although it could equally be configured to generate other characteristics thereof.

Figure 6:
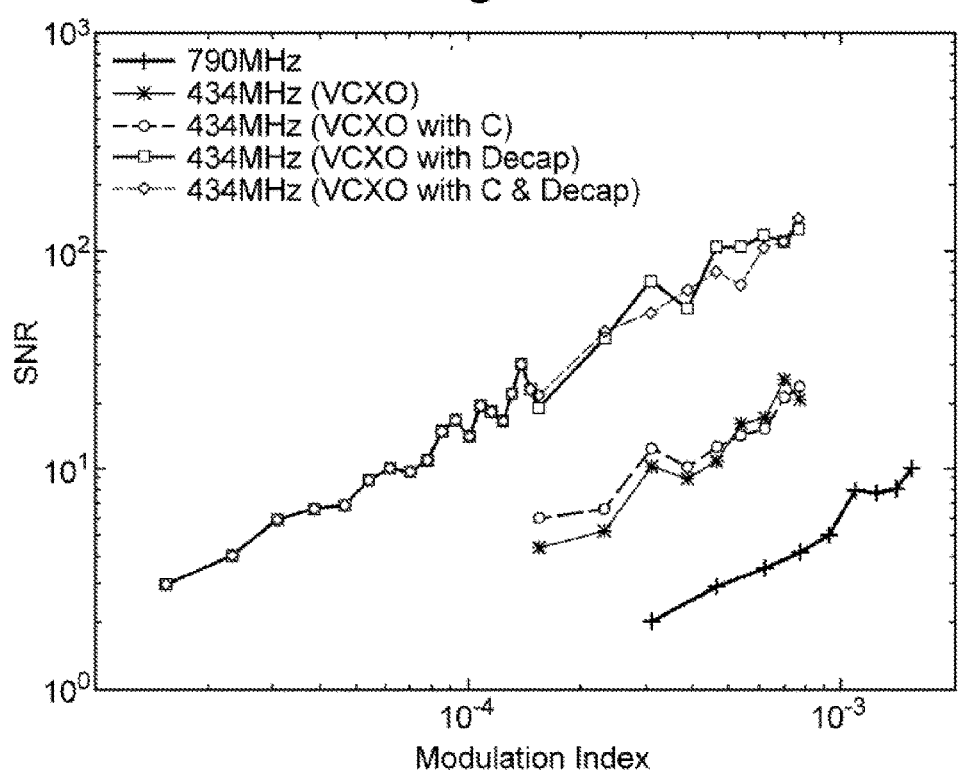
FIG. 6 is a graph of SNR against modulation index for some specific constructions of the signal processing apparatus.

This configuration of the FM demodulator 11 combining the PLL 60 and the lock-in amplifier 72 has been found to provide very sensitive detection of the Doppler component despite the relatively low signal level thereof. In frequency modulation terms, embodiments of the FM demodulator 11 have been found to be capable of detecting modulation indexes of the order of 10 parts in 1 million. This high sensitivity is achieved by the combination of the PLL 60, which effectively extracts the full set of Doppler components, and the lock-in amplifier 72 that subsequently extracts the desired one of the Doppler components, typically at the frequency fa of the fundamental frequency component. By way of example, FIG. 6 shows the performance of the first configuration (EM frequency of 790 MHz) and the second configuration (EM frequency of 434 MHz) with and without use of the capacitor in the low pass filter 68 (referred to as 'C' in FIG. 6) and with a separate decoupling capacitor (referred to as 'Decap' in FIG. 6) with a is lock-in time constant τ. For example, this shows that the second configuration can achieve a sensitivity index k (SNR/MI) of around 17000.

To facilitate the FM demodulation, the FM demodulator 11 is provided with the signal of the illuminating electromagnetic wave from the frequency source 7 and with the signal of the utilized frequency component of the AM waveform of the acoustic wave from the acoustic transducer apparatus 4.

The amplifier 10 and FM demodulator 11 may be formed by analog circuits, but digital circuits could alternatively be used for any part of the amplifier 10 and FM demodulator 11. For example, a digital implementation of the lock-in amplifier 72 is particularly advantageous when plural regions 5 are simultaneously imaged as discussed below.

The signal representing the phase and amplitude of the Doppler component derived by the FM demodulator 11, in particular output by the lock-in amplifier 72, are supplied to the digital signal processor 12 which processes those characteristics of the Doppler components. As the FM demodulator 11 detects characteristics of Doppler components at frequencies shifted from the frequency of the illuminating electromagnetic wave by frequencies of the frequency components of the AM waveform and multiples thereof, those characteristics are known to have been derived from the region 5 of the object 2 at the current location of the acoustic vibration. The digital signal processor 12 is supplied with information by the control unit 3 identifying the current location of the acoustic vibration. The digital signal processor 12 stores image data 13 representing those characteristics detected in respect of each location as the location is scanned over the object 2. The image data 13 may be stored, displayed and/or output from the signal processing apparatus 9.

The digital signal processor 12 may store only the actually derived values of the phase and amplitude or other characteristics. These vary in dependence on the properties of the object 2 at different locations as discussed above and therefore provide a useful image even without further processing.

Optionally, the digital signal processor 12 may further process the actually derived values of the phase and amplitude or other characteristics, on the basis of a model of the interaction between the acoustic vibration and the illuminating electromagnetic wave, to derive characteristics representing particular physical properties of the object 2 which are also stored as image data 13. Such processing may provide information on properties of the object 2 which are more useful than the phase and amplitude themselves. For example in the case of medical imaging, such processing may be used to characterise metabolite species which have known electromagnetic responses.

The digital signal processor 12 may be implemented by a computer apparatus executing an appropriate program, optionally being the same computer apparatus as used to implement the control unit 3.

The connection from the radio frequency source 7 to the FM demodulator 11 shown in FIG. 1 may be omitted in the case that the FM demodulator 11 has the construction shown in FIG. 5. However, in an alternative construction of the FM demodulator 11 in which the PLL 60 is replaced by a coherent detector, this connection is used to supply the coherent detector with the drive signal output by the radio frequency source 7 having the EM frequency of the illuminating electromagnetic wave. In this alternative, the coherent detector uses that signal to detect signals at the EM frequency and therefore produces an output signal of a similar form to the PLL 60. The acoustic transducer apparatus 4 and various variations thereof will now be described.

As previously mentioned, the acoustic transducer apparatus 4 provides acoustic vibration that is localized in a region 5 at a given time, that is localized in two dimensions in a region 5b that extends in the propagation direction or localized in three dimensions in a region 5a that is limited in the propagation direction. This may be achieved using a conventional apparatus that may provide a controllable focus or a fixed focus.

Figure 7:
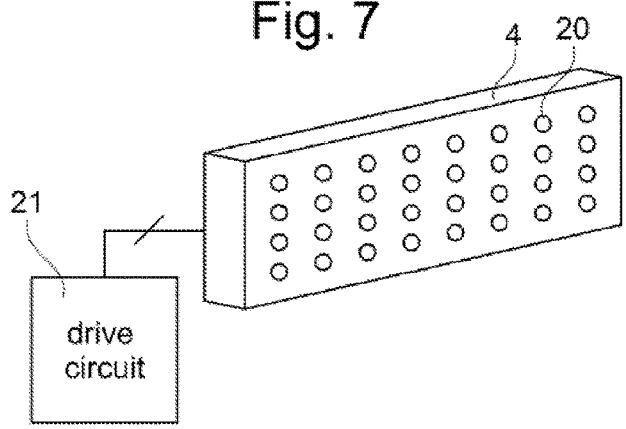
FIG. 7 is a perspective view of an acoustic transducer apparatus of the imaging system.

FIG. 7 shows a possible arrangement in which the acoustic transducer apparatus 4 comprises an array of transducers 20 which provide an electronically controllable focus at a region 5. In this case, the acoustic wave output by the array of transducers 20 may be a propagating beam. As known in the field of ultrasound imaging such beam-forming allows a high energy focus to be formed at a desired location. In the present method this means that the majority of the scattered electromagnetic wave contains information pertaining to the region 5 of focus.

To provide localization in two dimensions, the array of transducers 20 may apply the acoustic vibration as a continuous beam, so that the acoustic vibration is localized in space within the propagating beam in the two dimensions perpendicular to the direction of propagation. To provide localization in three dimensions, the array of transducers 20 may still apply the acoustic vibration as a beam, but as a beam that is not continuous, so that along the third dimension in the direction of propagation, the acoustic vibration is localized instantaneously as the acoustic wave propagates. The propagating beam may be a pulse which is localized in a single region 5 at a given time which region 5 propagates through the object 2 over time. Alternatively the propagating beam may have an AM waveform of varying frequency so that different frequencies are localized in different regions 5 simultaneously. Accordingly, the information supplied by the control unit 3 to the digital signal processor 12 indicates the timing of the propagating beam, thereby identifying the current location of the acoustic vibration.

In the case that the propagating beam has an AM waveform of varying frequency, one option is that the signal processing apparatus 9 is arranged to perform a Fourier Transform, or other transform, of the received scattered signal into the time domain. Due to the different frequencies of acoustic vibration being localized in different regions 5 simultaneously, such a transform generates the characteristics in respect of each of the different regions 5. In this way, a "movie" can be constructed and images as a function of time can be displayed with extremely high temporal/spatial resolution.

To form the propagating beam, the acoustic transducer apparatus 4 comprises a drive circuit 21 which provides a separate drive signal to each transducer 20 which drive signals vary in amplitude and/or phase and/or delay to form the focus at the desired region 5. Such formation of a beam from an array of transducers is known in itself, for example in the field of ultrasound imaging.

Figure 8:
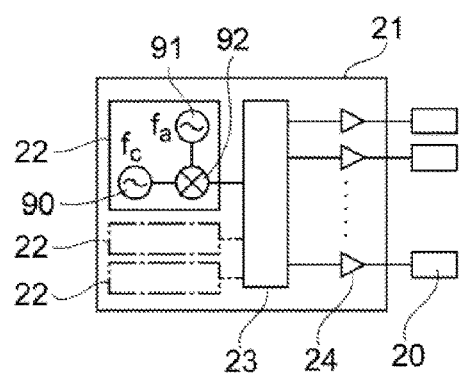
FIG. 8 is diagram of a drive circuit of the acoustic transducer apparatus.

As shown in FIG. 8, the drive circuit 21 includes a waveform generator 22 which generates an oscillating signal having a waveform corresponding to the desired waveform of the acoustic vibration and supplies it to a beamformer circuit 23. The beamformer circuit 23 may be implemented in analog or digital means. The waveform generator 22 comprises a carrier frequency source 90 that outputs a signal having the frequency fc of the carrier wave, and an AM waveform source 91 that outputs the AM waveform, which in the simplest case may comprise a fundamental frequency component of frequency fa. The waveform generator 22 also comprises a mixer 92 that mixes the two signals output by the carrier frequency source 90 and the AM waveform source 91 to derive the oscillating signal.

The beamformer circuit 23 derives a signal for each transducer 20 from the oscillating signal by modifying the amplitude and/or phase and/or delay by respective amounts that shape the overall acoustic vibration output from the acoustic transducer apparatus 4 into a beam. The beamformer circuit 23 operates under the control of the control unit 3 to provide a focus in a desired region 5. The drive circuit 21 also includes amplifiers 24 for amplifying the signal for each transducer 20 output by the beamformer circuit 23 to form the drive signal which is then supplied to the respective transducers 20.

Figure 9:
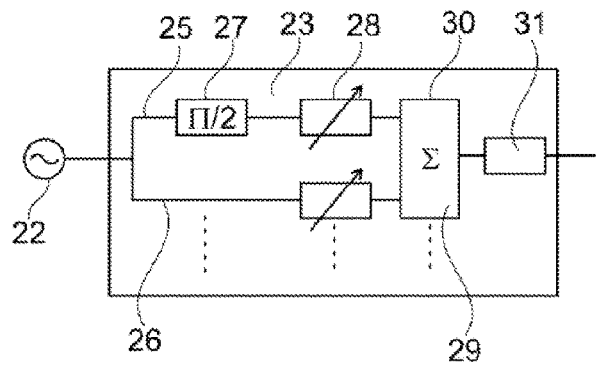
FIG. 9 is a diagram of a beamformer circuit of the drive circuit.

The beamformer circuit 23 may include programmable amplifiers (or attenuators) and/or phase shifters and/or delays to modify the oscillating signal. For example, the beamformer circuit 23 may employ a quadrature arrangement as shown in FIG. 9 in respect of each one of the transducers. This quadrature arrangement comprises an I-channel 25 and a Q-channel 26 each supplied with the oscillating signal from the waveform generator 22. The I-channel includes a $\tau/2$ phase delay 27 for phase-delaying the oscillating the oscillating signal so that the signals in the I-channel 25 and Q-channel 26 are in quadrature. The I-channel 25 and Q-channel 26 each include respective attenuators 27 and 28, the outputs of which are supplied to an adder 30 for adding the attenuated quadrature signals. The respective degrees of attenuation provided by each of the attenuators 27 and 28 may be controlled to thereby vary the amplitude and phase of the signal output by the adder 30. This signal output by the adder 30 is optionally provided to a variable delay circuit 31 which may be varied to control the delay of the drive signal.

The drive circuit 21 may be formed by analog circuits, but digital circuits could alternatively be used for any part thereof.

Figure 10:
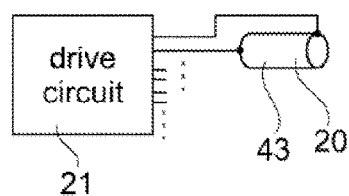
FIG. 10 is a perspective view of a transducer of the acoustic transducer apparatus.

Each transducer 20 may be formed as shown in FIG. 10 by a piece 43 of piezoelectric material (or other electroactive material). The drive signal from the drive circuit 21 is applied across the piece 43 of piezoelectric material which vibrates in response thereto thereby generating an acoustic wave. The piece 43 of piezoelectric material is shown as being cylindrical but may be shaped to direct the generated acoustic wave.

In FIG. 7, the array of transducers 20 is illustrated as a 2D planar array, but in general any arbitrary form of array may alternatively be used, for example a 1D linear or conformal array, a curved or conformal 2D array, a 3D array, or plural arrays on different sides of the object 2.

As an alternative to forming a beam, this acoustic transducer apparatus 4 comprising the array of transducers 20 may apply the acoustic vibration as a spot which is continuously localized in space in three dimensions.

Using this acoustic transducer apparatus 4 comprising an array of transducers 20, the location of the region 5 at which the acoustic vibration is localized may be scanned over the object 2 under electronic control to derive information on different regions 5 and thereby build up an image of the object 2.

In the case that the acoustic vibration is localized in two dimensions, then the image is a two dimensional image (or shadow image) whose pixels contain information from the entirety of the region 5b that extend through the object 2 along the propagation direction of the acoustic vibration. In this case, a three dimensional image can be built up by moving the acoustic transducer apparatus 4 and transmitter antenna 6 around the object 2 under examination and taking a series of images with different angles of incidence. Then the series of images may be transformed into a three dimensional image using similar transforms to those conventional for other types of imaging such as computed tomography (CT) scanning.

In the case that the acoustic vibration is localized in three dimensions, then a three-dimensional image may be derived by scanning the region 5a in three dimensions.

Such scanning could also be achieved using an acoustic transducer apparatus 4 which has a fixed focus, by physically moving the acoustic transducer apparatus 4.

As previously mentioned, in the simplest embodiment, the acoustic vibration is localized in a single region 5 at a given time, the acoustic vibration being applied to regions 5 at a plurality of different locations successively.

In more complicated embodiments, the acoustic vibration is localized in plural regions 5 at different locations simultaneously. In this case, the acoustic vibration has an AM waveform including utilized frequency components, normally the fundamental frequency components, having different frequencies in different regions 5.

One option is to use the acoustic transducer apparatus 4 comprising an array of transducers 20 as described above but modified to simultaneously produce plural propagating beams with AM waveforms of different frequencies. This may be achieved by replicating the circuitry of the drive circuit 21, as described above and shown in FIG. 8, in respect of each of the different frequencies used. The drive signals in respect of each frequency may be summed and applied to the respective transducers 20.

Whilst it would be possible to replicate the entire circuitry of the drive circuit 21 described above, more conveniently, merely the waveform generator 22 is replicated, as shown in dotted outline in FIG. 8. The same or different carrier frequencies fc may be used to provide localization in each region 5 but in the case of using the same carrier frequencies fc then a common carrier frequency source 90 may be provided. In the case that the waveform generator 22 is replicated, the beamformer circuit 23 performs two functions. Firstly, in respect of each waveform generator 22, the beamformer circuit 23 derives a signal for each transducer 20 from the oscillating signal by modifying the amplitude and/or phase and/or delay suitable for producing a beam directed to the respective region. Secondly, the beamformer circuit 23 sums the derived signals in respect of each transducer 20 to derive a summed signal that is supplied to the respective amplifiers 24. As the acoustic vibration has different frequencies in different regions 5, the scattered electromagnetic wave has Doppler components of different frequencies generated in the different regions 5, each having frequencies shifted from the frequency of the illuminating electromagnetic wave by the different frequencies of the frequency component of the AM waveform of the acoustic vibration (and multiples thereof). The signal processing apparatus 9 is therefore arranged to detect and derive characteristics of the different Doppler components which are known to have been generated at the different locations of the regions 5. This may be achieved by the signal processing apparatus 9 being arranged as described above but within the FM demodulator 11 replicating the lock-in-amplifier 72 in respect of each of the acoustic frequencies used. This is discussed in further detail below.

In this manner, characteristics of the Doppler components and therefore image data 13 may be simultaneously be derived in respect of plural regions 5. Many regions 5 may be simultaneously imaged in this manner. This approach is limited by the ability of the signal processing apparatus 9 to discriminate between Doppler components of different frequencies.

In some arrangements, plural regions 5 are simultaneously imaged allowing an image to be derived without scanning the regions 5. In other arrangements, plural regions 5 are simultaneously imaged but then the regions 5 are scanned to image other areas of the object 2. For example, one particular embodiment may employ a plurality of propagating beams arranged in a 1D (or 2D) array to simultaneously image a 1D (or 2D) slice which propagates through the object 2 allowing successive slices to be imaged, thereby building up a 2D (or 3D) image in a similar manner to conventional medical ultrasound imaging as employed for example in obstetric sonography. Thus, the use of plural regions 5 allows an image to be scanned more quickly than if a single region 5 is used, thereby improving the image acquisition period. This is a particular advantage in the case of imaging a living object as it reduces the length of time for which the object needs to be stationary.

Alternatively, the system 1 may be implemented to investigate the properties of the object 2 in a single region 5 without providing imaging across the object 2. In this case, acoustic vibration is applied to just a single region 5. This may be achieved with the system 1 as described above but modifying the control implemented by the control unit 3. Alternatively, the system 1 may be simplified, for example using an acoustic transducer apparatus 4 having a fixed focus because scanning is not required.

When investigating the properties of the object 2 in a single region 5, it is particularly advantageous to use acoustic vibrations of different frequencies and/or with an illuminating electromagnetic wave of different frequencies, as described above. The different frequencies may be applied at different times or simultaneously. In the latter case it is possible to tune the system 1 to simultaneously investigate a wide range of frequencies without needing to use the different frequencies to obtain information on regions 5 at different locations as is necessary with some imaging implementations.

The size and detailed construction of the system 1 will depend on the field of application. For example for use in medical imaging, the system 1 might be realised as a dedicated device in which the acoustic transducer apparatus 4 is similar to an ultrasound head in a conventional ultrasound imaging apparatus. In this case, the transmitter antenna and receiver antenna might be integrated into the same ultrasound head.

Optionally, the system 1 might additionally incorporate an acoustic system 14 connected to the acoustic transducer apparatus and arranged to receive a reflected acoustic wave from each of the regions 5 and thereby to derive acoustic image data 15 with derivation of the image data 13 by the signal processing apparatus 9. The acoustic system 14 may be arranged as conventional ultrasound imaging apparatus, thereby allowing the present method to be integrated with conventional ultrasound imaging. The acoustic image data 15 and the image data 13 may be registered with each other in space and time, for example using conventional image registration techniques, allowing the system 1 to simultaneously produce two different types of image. This is advantageous in many fields, for example as a real time system for dynamic diagnostics and monitoring.

Similarly the system 1 might be integrated with an ultrasound treatment system, allowing monitoring of state of the object 2 during treatment.

Figure 11:
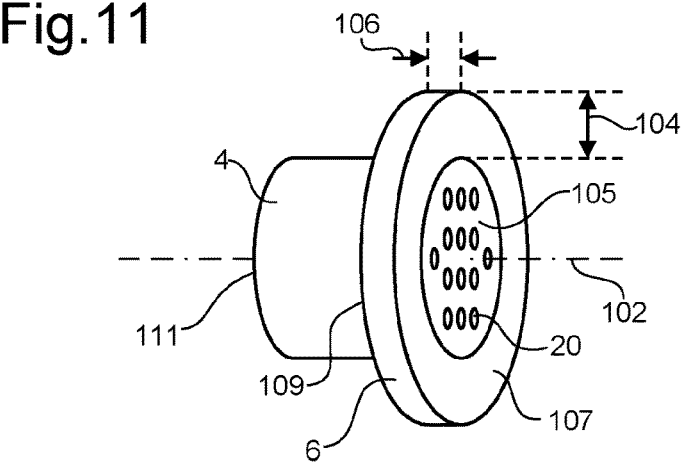
FIG. 11 is a perspective view of an acoustic transducer apparatus 4 positioned within the aperture of an antenna coil.
Figure 12:
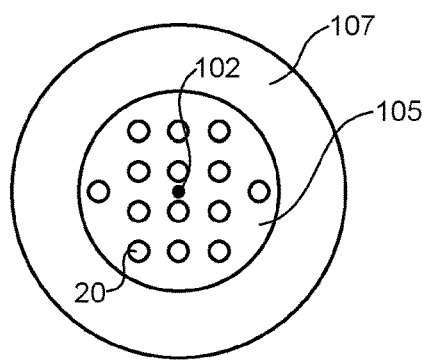
FIG. 12 is a front end view of the transducer/coil arrangement of FIG. 11.

FIGS. 11 and 12 depict an arrangement comprising an acoustic transducer apparatus 4 and an antenna coil 6. In an embodiment, the coil 6 is a common coil for use both as a transmitter arrangement and as a receiver arrangement. In other embodiments, the coil 6 is used as a transmitter arrangement only or as a receiver arrangement only. FIG. 11 is a perspective view of the arrangement. FIG. 12 is a front end view.

In the embodiment shown, the coil 6 surrounds an axis 102 along which at least a portion of the acoustic vibration from the acoustic transducer apparatus 4 is output. The coil 6 comprises a single turn or multiple turns. In an embodiment, the single turn or one or more of the multiple turns surrounds the axis 102.

In the embodiment shown, the coil 6 surrounds the axis through substantially 360 degrees. However, this is not essential. In other embodiments, the coil 6 may surrounds the axis only partially, for example through 180 degrees or more, optionally 270 degrees or more, optionally 350 degrees or more, optionally 359 degrees or more.

In an embodiment, the coil 6 is configured such that a principle transmitting and/or receiving direction (e.g. the direction along which transmission or detection of electromagnetic waves is strongest) is parallel to or co-axial with the output from at least a portion of the acoustic transducer apparatus.

In the example shown, a leading face 105 of the acoustic transducer apparatus 4 is substantially co-planar with a leading face 107 of the coil 6. This may be desirable where the coil 6 is to be brought into contact with the surface of the body containing the object to be investigated at the same time as the acoustic transducer apparatus 4. In such an embodiment, the part of the acoustic transducer apparatus 4 immediately adjacent to the leading face 105 is also surrounded circumferentially by the coil 6. However, this is not essential. In other embodiments, the leading face 105 of the acoustic transducer apparatus 4 protrudes forwards of the leading face 107 of the coil 6 or is recessed backwards from the leading face 107. The acoustic transducer apparatus 4 may even be positioned completely outside of the coil 6 (i.e. such that the leading face 105 of the acoustic transducer apparatus 4 is axially behind the trailing face 109 of the coil 6 or a trailing edge 111 of the acoustic transducer apparatus 4 is completely in front of the leading face 107 of the coil 6).

Typically the coil 6 will be tuned to operate most efficiently at one or more frequencies or frequency ranges. The central aperture of the coil 6 is designed respectively to intercept and generate the magnetic field lines of the incident and transmitted waves. According to the present invention, the space provided by the aperture is exploited to locate the acoustic transducer apparatus 4 in a compact and efficient manner. In particular, this arrangement allows the "look direction" of the coil 6 (axis 102 in the example shown) to be substantially parallel, or even co-axial, with the output direction of part or all of the acoustic vibration output from the acoustic transducer apparatus 4. Thus, the Doppler return signal is maximized as the induced motion in the object being imaged will be substantially parallel to the direction of propagation of the electromagnetic wave.

Specifically, according to an embodiment the coil 6 is configured to have at least one turn that surrounds an axis along which at least a portion of the acoustic vibration from the acoustic transducer apparatus 4 is output (for example, the axis along which acoustic vibrations are output from one of a plurality of transducers 20 in the case where the acoustic transducer apparatus 4 comprises an array of transducers 20).

The detailed construction of the coil 6 can be varied according to the particular circumstances in which the imaging is to be applied. However, it is beneficial in a wide range of situations to construct the coil 6 so that one or more of the turns of the coil each comprise at least two conductor sections that are connected together in series by a capacitor.

Figure 13:
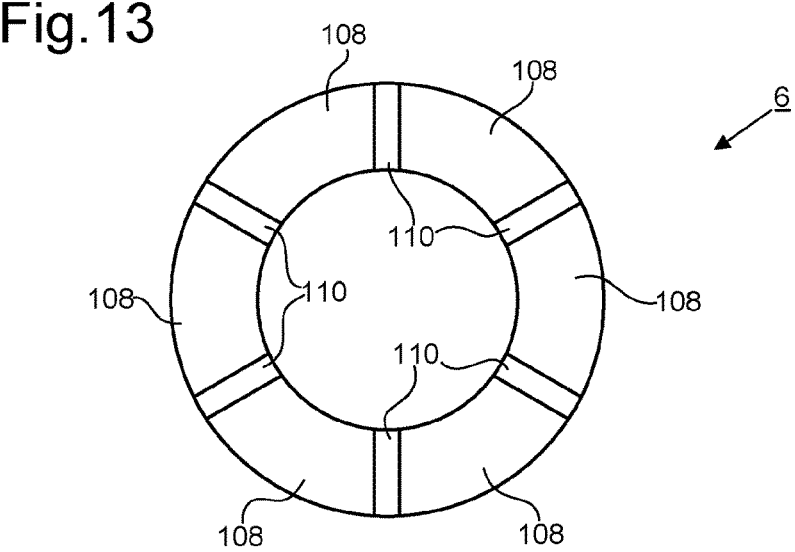
FIG. 13 depicts an antenna coil comprising a plurality of circumferential conducting sections separated by capacitors.

FIG. 13 is a schematic sectional view looking along the axis of the coil 6. The coil shown comprises a turn having six conducting sections 108 connected together in series by six capacitors 110. In the embodiment shown, the conducting sections 108 and capacitors 110 are all identical but this is not essential. Additionally, fewer than six or more than six conducting sections and/or capacitors may be provided. In an embodiment, one or more of the capacitors is tunable to allow the frequency response of the coil 6 to be fine tuned.

The effect of constructing the coil 6 from conducting sections 108 connected in series with capacitors 110 is to allow the physical size of the coil 6 to be reduced while maintaining the operating frequency within a useful range of frequencies (typically within the tens or hundreds of megahertz).

The cross-sectional profile of conducting portions of the coil 6, for example the cross-section profile of conducting sections 108 in an embodiment of the type shown in FIG. 13, can in general take a variety of forms. However, it is generally desirable for efficiency to achieve a relatively high electrical conductivity. A high electrical conductivity can be achieved by providing a large cross-sectional area. However, space considerations may limit the choice of cross-section. For example, circular cross-sectioned wire will tend to become unacceptably bulky when the diameter is made sufficiently large to achieve the desired efficiency. According to an embodiment, the cross-section of the coil 6 conducting is made relative wide and thin, in the manner of a tape. In this way, a relatively large cross-sectional area can be achieved without the associated height penalty. Such tapes can be oriented perpendicular or parallel to the plane of propagation of the acoustic vibration. However, it is advantageous in many contexts for the tape to be perpendicular as the structure can then lie flat against the surface of the body (e.g. the human or animal body) that contains the object to be imaged.

Specifically, according to an embodiment, as illustrated in FIG. 11, the coil 6 may be configured to have at least one conducting section with a thickness 106 in a direction parallel to a direction of output 102 of acoustic vibration that is smaller than the thickness 104 perpendicular to the direction of output 102 of acoustic vibration.

In an embodiment, the coil 6 is fixed (e.g. glued) to the body containing the object to be imaged.

In the embodiment discussed with reference to FIGS. 11 to 13 the coil 6 has a substantially circular form (when viewed along the axis of the coil 6). In other embodiments a different shape may be used, for example substantially oval, substantially ellipsoidal, substantially polygonal, or an irregular shape. In an embodiment the shape of the coil is adapted to the requirements of the acoustic transducer apparatus 4. For example, if the acoustic transducer apparatus 4 is preferably provided in rectangular form, the coil 6 may also be provided in a corresponding rectangular form.

In the embodiments discussed above with reference to FIGS. 11 to 13, the coil 6 is substantially planar. However, this is not essential. In other embodiments, the coil 6 is non-planar. For example, when viewed in at least one direction perpendicular to the direction of acoustic vibration propagation the coil 6 may comprise at least one portion that is at an oblique angle to, and/or portions that are at different angles to, the direction of acoustic vibration propagation (rather than all portions of the coil being at the same angle to, for example 90 degrees to, the direction of propagation).

In an embodiment, the coil 6 comprises a curved portion when viewed in at least one direction perpendicular to the direction of acoustic vibration propagation. In an embodiment, the coil 6 is curved so as to substantially conform with the shape of a portion of the body against which, or in close proximity directly adjacent to which, the coil 6 will be positioned to carry out imaging, or at least to conform to a greater extent than would be possible with a planar coil 6.

Figure 14:
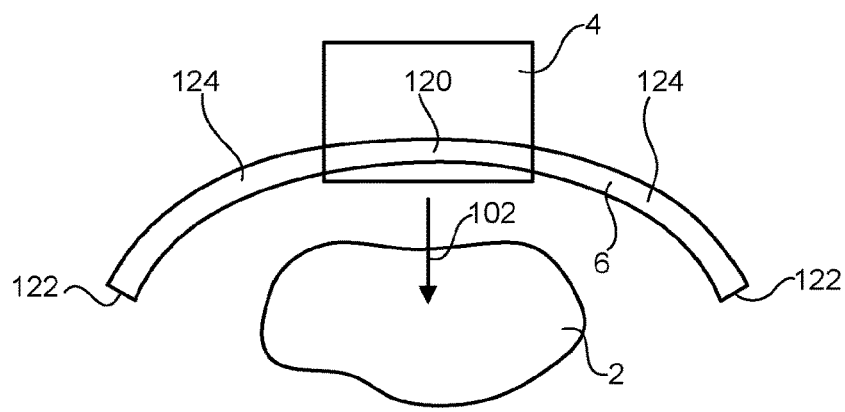
FIG. 14 is a top view of a transducer apparatus and a non-planar coil.
Figure 15:
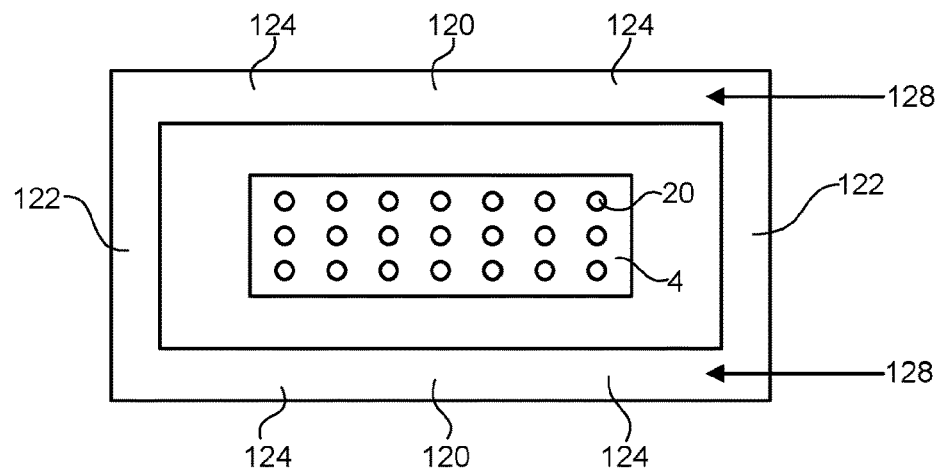
FIG. 15 is a front view of the transducer apparatus and non-planar coil of FIG. 14.

FIGS. 14 and 15 depict an embodiment comprising a non-planar, "conforming" coil 6. FIG. 14 is a top view, looking along a direction perpendicular to the direction 102 of acoustic vibration propagation output from the acoustic transducer apparatus 4. FIG. 15 is a front view along the direction of acoustic vibration propagation. As can be seen from FIG. 14 the coil 6 comprises portions that are at an oblique angle to the direction 102. The top and bottom bars 128 of the coil 6 are curved, such that in FIG. 15 the central region 120 is further back into the page than the obliquely angled regions 124 either side. In the embodiment shown, the side bars 122 are substantially straight and lie in the same plane. However this is not essential and the side bars could also be curved.

The coil 6 may be seen as "conforming" to the shape of the body 2 because it is shaped in a manner which enables the average distance of the coil 6 from the surface of the body 2 to be less than would be the case if the coil 6 was planar. In other words, the shape of the conforming coil 6 is more similar to the shape of the surface of the body against which it is to be brought than a planar coil 6 would be. In an embodiment, the coil 6 is shaped so that when placed against the body a majority of the coil is substantially parallel to the surface of the body.

Configuring the antenna coil to conform to the shape of the body is one way in which the response of the coil can be focused preferentially onto a given volume within the body. Focussing the response effectively reduces the illuminated volume in the body. Reducing the illuminated volume makes it possible to reduce the total power into the body. In addition, the return level of the unmodulated electromagnetic signal can be kept low. The sensitivity of the system is controlled in part by the ratio of the modulated return to that of the unmodulated return. Therefore the lower the level of the unmodulated return the better the sensitivity of the coil and associated receiver arrangement. In addition, thermal and other noise sources are spatially filtered out where they originate from regions that are outside of the volume of interest.

It is important that the coil 6 is well matched to the body being investigated. A shaped coil facilitates this process because it can be fitted more effectively against the body. The fitting allows more of the coil 6 to be brought into close proximity and/or contact with the surface of the body. Alternatively or additionally, the fitting enables the coil 6 to be brought against the surface of the body more repeatably. The coil 6 can thus be brought into a good position more easily and will tend to be more stable in that position, thus improving reliability and repeatability.

In an embodiment, the coil 6 is shaped so that a majority of a leading face of the coil 6 can be brought into contact with the surface of the body to be investigated at the same time as a leading face of the acoustic transducer apparatus is in contact with the surface. Optionally, this is achieved in a hand-held device.

Figure 16:
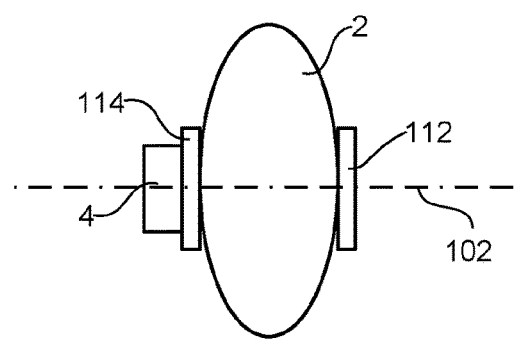
FIG. 16 depicts application of a system comprising separate transmitter and receiver arrangements to a body comprising an object to be imaged.

In the embodiments described with reference to FIGS. 11 to 15, a single antenna coil acts both as transmitter and receiver. In an embodiment of this type, a directional coupler 8 is provided to separate out the transmitted and received signals. However, it is also possible that two separate coils can be used as separate transmitter and receivers. FIG. 16 illustrates a schematic embodiment of this type. Here, a transmitter coil 114 is provided separately from a receiver coil 112. The transmitter and receiver coils 114, 112 are positioned opposite to each other on either side of a body 2 containing the object to be imaged. The acoustic transducer apparatus is provided within the transmitter coil 114 in the embodiment shown. The receiver coil 112 is positioned opposite to the transmitter coil 114 and surrounds the axis of the acoustic transducer apparatus 4. In the embodiment shown either or both of the transmitter coil 114 and receiver coil 112 may surround the axis 102 along which at least a portion of the acoustic vibration from the acoustic transducer apparatus 4 is output. In an alternative embodiment, the coil 114 is configured to receive electromagnetic radiation and the coil 112 is configured to transmit the electromagnetic radiation.

Any of the coils mentioned above could be single turn coils or multiple turn coils.

The invention claimed is:

1. A system for investigating physical properties of an object, the system comprising:
   an acoustic transducer apparatus arranged to apply to the object acoustic vibration localized in two or three dimensions in a region in the object;
   a transmitter arrangement arranged to illuminate the object with an illuminating electromagnetic wave having a frequency in a range extending down from 30 THz simultaneously with the application of acoustic vibration, the vibration direction of the acoustic vibration having a component parallel to the propagation direction of the illuminating electromagnetic wave so that the vibration of the object caused by the acoustic vibration in the region generates a scattered electromagnetic wave including a set of Doppler components shifted from the frequency of the illuminating electromagnetic wave by frequencies of the vibration of the object caused by the acoustic vibration and multiples thereof;
   a receiver arrangement arranged to receive the scattered electromagnetic wave generated in the region; and
   a signal processing apparatus arranged to derive, from the received scattered electromagnetic wave generated in the region, data representing at least one characteristic of the Doppler components,
   wherein the transmitter arrangement or the receiver arrangement comprises an antenna coil surrounding, through at least 180 degrees, an axis along which at least a portion of the acoustic vibration from the acoustic transducer apparatus is output, and
   wherein the coil is fixedly connected to the acoustic transducer apparatus and configured to illuminate the object with the coil and the acoustic transducer apparatus located on a same side of the object.

2. A system according to claim 1, wherein the coil is common to both the transmitter arrangement and the receiver arrangement.

3. A system according to claim 1, wherein:
   a principle transmitting or receiving direction of the coil is parallel to or co-axial with the output from at least a portion of the acoustic transducer apparatus.

4. A system according to claim 1, wherein the coil comprises at least two conductor sections connected together by a capacitor.

5. A system according to claim 1, wherein the coil comprises a conducting section having a thickness that is smaller in a direction parallel to the average output direction of acoustic vibration than in a direction perpendicular to the average output direction of acoustic vibration.

6. A system according to claim 1, wherein the coil has one of the following shapes when viewed along a direction of output of acoustic vibration: substantially circular, substantially oval, substantially ellipsoidal, substantially polygonal.

7. A system according to claim 1, wherein the coil is substantially planar.

8. A system according to claim 1, wherein the coil is substantially non-planar.

9. A system according to claim 1, wherein the coil comprises a plurality of turns.

10. A system according to claim 1, wherein the coil is shaped to obtain a response preferentially from a predetermined volume in front of the antenna.

11. A system according to claim 1, wherein the coil is shaped to illuminate preferentially a predetermined volume in front of the antenna.

12. A system according to claim 1, wherein the acoustic vibration comprises a carrier wave that is amplitude modulated by an AM waveform.

13. A system according to claim 12, wherein the signal processing apparatus is configured to detect, from the received, scattered electromagnetic wave, a Doppler component shifted from the frequency of the illuminating electromagnetic wave by the frequency of a frequency component of the AM waveform, and to output a signal representing at least one characteristic of the detected Doppler component.

14. A system according to claim 1, wherein the coil surrounds the axis through at least 350 degrees.

15. A method of investigating physical properties of an object, comprising:
    using an acoustic transducer apparatus to apply to the object acoustic vibration localized in two or three dimensions in a region in the object;
    illuminating the object with an illuminating electromagnetic wave having a frequency in a range extending down from 30 THz simultaneously with the application of acoustic vibration, the vibration direction of the acoustic vibration having a component parallel to the propagation direction of the illuminating electromagnetic wave so that the vibration of the object caused by the acoustic vibration in the region generates a scattered electromagnetic wave including a set of Doppler components shifted from the frequency of the illuminating electromagnetic wave by frequencies of the vibration of the object caused by the acoustic vibration and multiples thereof;
    receiving the scattered electromagnetic wave generated in the region;
    deriving, from the received scattered electromagnetic wave generated in the region, data representing at least one characteristic of the Doppler components, wherein the illuminating or receiving comprises using an antenna coil that surrounds, through at least 180 degrees, an axis along which at least a portion of the acoustic vibration from the acoustic transducer apparatus is output, and wherein the coil is fixedly connected to the acoustic transducer apparatus and illuminates the object while the coil and the acoustic transducer apparatus are located on a same side of the object.

16. A method according to claim 15, wherein the coil is placed against the skin of a human or animal in order to investigate physical properties of an object comprising tissue of the human or animal.

17. A method according to claim 16, wherein the coil is shaped so as to conform with the part of the human or animal against which the coil is placed.

18. A method according to claim 16, wherein the illuminating uses a first of said antennas that is placed against a first part of the human or animal body and the receiving uses a second of said antennas that is placed against a second part of the human or animal, different from the first part.

19. A method according to claim 18, wherein the first and second parts of the human or animal body are on opposite sides of the human or animal body.

* * * * *